US00PP11174P

United States Patent [19]

VandenBerg

[11] Patent Number: Plant 11,174

[45] Date of Patent: Jan. 11, 2000

[54] CHRYSANTHEMUM PLANT NAMED 'SOLEDAD'

[75] Inventor: Cornelis P. VandenBerg, Salinas, Calif.

[73] Assignee: Yoder Brothers, Inc., Barberton, Ohio

[21] Appl. No.: 09/113,139

[22] Filed: Jul. 9, 1998

[51] Int. Cl.[7] ..... A01H 5/00

[52] U.S. Cl. ..... Plt./286

[58] Field of Search ..... Plt./286, 297

*Primary Examiner*—Howard J. Locker

*Attorney, Agent, or Firm*—C. A. Whealy

[57] ABSTRACT

A distinct cultivar of Chrysanthemum plant named 'Soledad', characterized by its compact and uniformly mounded plant habit; freely branching habit, dense plants; uniform and early flowering; anemone spraytype inflorescences that are about 5.1 cm in diameter; attractive light pink to white-colored ray florets and red purple-tipped disc florets; numerous inflorescences per plant; and good post-production longevity with inflorescences and leaves maintaining good substance and color for about three of four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Soledad.

The new Chrysanthemum is a product of a planned breeding program conducted by the inventor in Salinas, Calif. The objective of the breeding program is to create new pot-type Chrysanthemum cultivars having desirable inflorescence forms and floret colors and excellent post-production longevity.

The new Chrysanthemum originated from a cross made by the breeder in July, 1993, in Salinas, Calif., of the *Dendranthema grandiflora* cultivar Penny Lane (disclosed in U.S. Plant Pat. No. 6,238) as the male, or pollen, parent with a proprietary Chrysanthemum seedling selection code No. 91-417001 as the female, or seed, parent.

The new Chrysanthemum was discovered and selected by the inventor as a flowering plant within the progeny of the stated cross in a controlled environment in Salinas, Calif., in March, 1994. The selection of this plant was based on its desirable inflorescence form and floret colors and excellent post-production longevity.

Asexual reproduction of the new Chrysanthemum by terminal cuttings harvested in a controlled environment is Salinas, Calif., has shown that the unique features of this new Chrysanthemum are stable and reproduced true to type in successive generations.

SUMMARY OF THE INVENTION

The cultivar Soledad has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Soledad'. These characateristics in combination distinguish 'Soledad' as a new and distinct Chrysanthemum:

1. Compact and uniformly mounded plant habit.
2. Freely branching habit, dense plants.
3. Uniform and early flowering.
4. Anemone spray-type inflorescences that are about 5.1 cm in diameter.
5. Attractive light pink to white-colored ray florets and red purpletipped disc florets.

6. Numerous inflorescences per plant.
7. Good postproduction longevity with inflorescences and leaves maintaining good substance and color for about three or four weeks in an interior environment.

The new Chrysanthemum can be compared to the Chrysanthemum cultivar Bi-Time (disclosed in U.S. Plant Pat. application Ser. No. 08/232,653, now abandoned). However in side-by-side comparisons in Salinas, Calif., and Leamington, Ontario, Canada, under commercial practice, plants of the new Chrysanthemum differed from plants of the cultivar Bi-Time in the following characteristics:

1. Plants of the new Chrysanthemum are more compact and not as open as plants of the cultivar Bi-Time.
2. Plants of the new Chrysanthemum have smaller inflorescences than plants of the cultivar Bi-Time.
3. Inflorescences of plants of the new Chrysanthemum have shorter but more numerous ray florets than inflorescences of plants of the cultivar Bi-Time.
4. Disc floret color of plants of the new Chrysanthemum is lighter purple than disc floret color of plants of the cultivar Bi-Time.
5. Plants of the new Chrysanthemum have shorter peduncles than plants of the cultivar Bi-Time.

A detailed comparison of plants of the new Chrysanthemum and the cultivar Bi-Time appears in Chart A at the end of the specification.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Soledad'.

The photograph at the bottom of the first sheet is a close-up view of typical inflorescences of plants of 'Soledad'.

The photograph at the top of the second sheet is a close-up view of upper and lower surfaces of typical inflorescences (top) and leaves (bottom) of plants of 'Soledad'.

The photograph at the bottom of the second sheet comprises a side perspective view of typical plants of 'Soledad' (left) and 'Bi-Time' (right) showing the differences in plant size, shape, inflorescence size and disc floret color. Floret and foliage colors in the photographs may appear different from the actual colors due to light reflectance.

DETAILED BOTANICAL DESCRIPTION

In the following description, color references are made to The Royal Horticulural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrotted cuttings were directly stuck in a 15-cm container and pinched once. Measurments and numerical values represent averages of typical flowering plants.

Botanical classifications: *Dendranthema grandiflora* cultivar Soledad.

Commerical classification: Anemone spray-type pot chrysanthemum.

Parentage:

*Male or pollen parent.*—*Dendranthema grandiflora* cultivar Penny Lane, disclosed in U.S. Plant Pat. No. 6,238.

*Female or seed parent.*—Proprietary *Dendranthema grandiflora* seedling selection code number 91-417001.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous anemone spray-type pot Chrysanthemum. Inverted triangle. Stems initially upright, then somehwat spreading giving a uniformly mounded appearance to the plant. Freely branching; about four to five lateral branches develop after removal of terminal apex (pinching), dense and full plants.

*Plant height.*—Compact, about 20 cm.

*Plant width.*—About 34 cm.

*Foliage description.*—Arrangement: Alternate. Length: About 5.7 cm. Width: About 3.8 cm. Apex: Mucronate. Base: Attenuate. Margin: Palmately lobed, sinuses between lateral lobes parallel to divergent. Texture: Upper and lower surface slightly pubescent. Veins prominent on lower surface. Petiole length: About 1.1 cm Color: Young foliage upper surface: 147A. Young foliage lower surface: Darker than 147B. Mature foliage upper surface: 147A. Mature foliage lower surface: Slightly darker than 147B. Venation upper surface: 147A/147B. Venation lower surface: 147B.

Inflorescence description:

*Appearance.*—Anemone spray-type inflorescence form with oblong shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to aboout two weeks of long day/short night conditions after planting followed by photoinductive short day/long night conditons flower about eight weeks later.

*Postproduction longevity.*—Inflorescences and leaves will maintain good color and substance for about three or four weeks in an interior environment.

*Quantity of inflorescences.*—About six inflorescences per terminal with about 27 inflorescences per plant.

*Inflorescence bud.*—Height: About 6 mm. Diameter: About 8 mm. Color: 143A.

*Inflorescence size.*—Diameter: About 5.1 cm. Depth (height): About 1.5 cm. Diameter of disc: About 3.2 cm

*Ray florets.*—Shape: Oblong with short corolla tube. Aspect; Straight, flat. Length: About 2.4 cm. Width: About 8 mm. Apex: Acute or emarginate. Margin: Entire. Texture: Smooth, glabrous. Number of ray florets per inflorescence: About 30. Color: When opening, upper surface: 76D to white. When opening, lower surface: 76A to 76D. Fully opened, upper surface: 76D to white. Fully opened, lower surface: 76D to white with purple, 75A to 76D, central longitudinal streaks.

*Disc florets.*—Shape: Enlarged tubular. Apex: Dentate, flared. Length: About 1.7 cm. Width: Apex: About 5 mm. Base: About 1.5 mm. Number of disc florets per inflorescence: About 128. Color: Immature, apex: Close to 61A. Mature: Apex: Close to 61A. Mid-Section: White, 155D. Base: Light green, 144A.

*Peduncle.*—Aspect: Flexible, strong, angled about 50° to stem. Length: First penduncle: About 1.5 cm. Fourth penduncle: About 3.2 cm. Texture: Pebescent. Color: 143A.

*Reproductive organs.*—Androecium: Present on disc florets only. Anther color: 9A. Pollen: Amount: Moderate to low. Color: 9A. Gynoecium: Present on both ray and disc florets.

Disease resistance: No known Chrysanthemum diseases observed to date on plants grown under commercial greenhouse conditions.

Seed production: Seed production has not been observed.

CHART A

| CHARACTERISTIC | 'SOLEDAD' | *BI-TIME'* |
|---|---|---|
| PLANT HEIGHT | About 20 cm | About 28 cm |
| PLANT WIDTH | About 34 cm | About 42 cm |
| LEAF SINUSES | Parallel to divergent | Overlapping |
| INFLORESCENCE DIAMETER | About 5.1 cm | About 5.6 cm |
| INFLORESCENCE HEIGHT | About 1.5 cm | About 1.3 cm |
| DIAMETER OF DISC | About 3.2 cm | About 2.8 cm |
| QUANTITY OF RAY FLORETS PER INFLORESCENCE | About 30 | About 22 |
| RAY FLORET LENGTH | About 2.4 cm | About 2.7 cm |
| RAY FLORET WIDTH | About 8 mm | About 8 mm |
| DISC FLORET LENGTH | About 1.7 cm | About 1.3 cm |
| DISC FLORET COLOR, IMMATURE, APEX | Close to 61A | Close to 59A |
| DISC FLORET COLOR, MATURE, APEX | Close to 61A | Close to 71A |
| FIRST PEDUNCLE LENGTH | About 1.5 cm | About 2.9 cm |
| FOURTH PEDUNCLE LENGTH | About 3.2 cm | About 5.2 cm |

It is claimed:

1. A new and distinct cultivar of Chrysanthemum plant named 'Soledad', as illustrated and described.

* * * * *

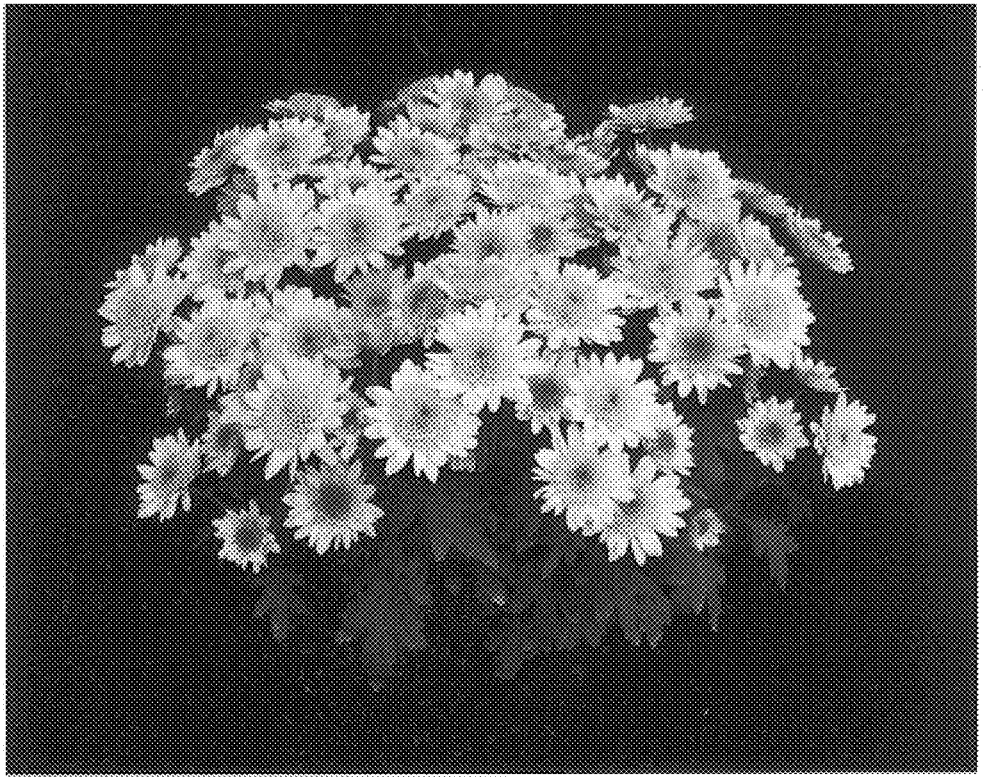
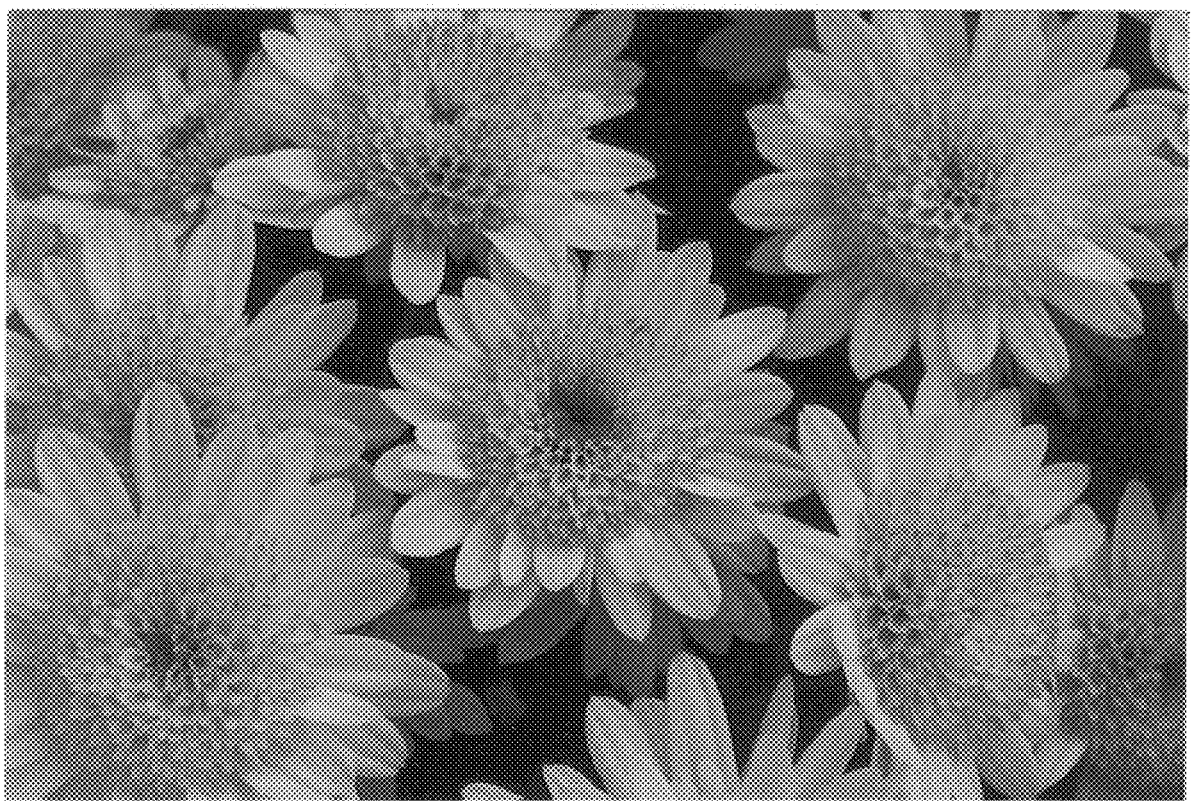

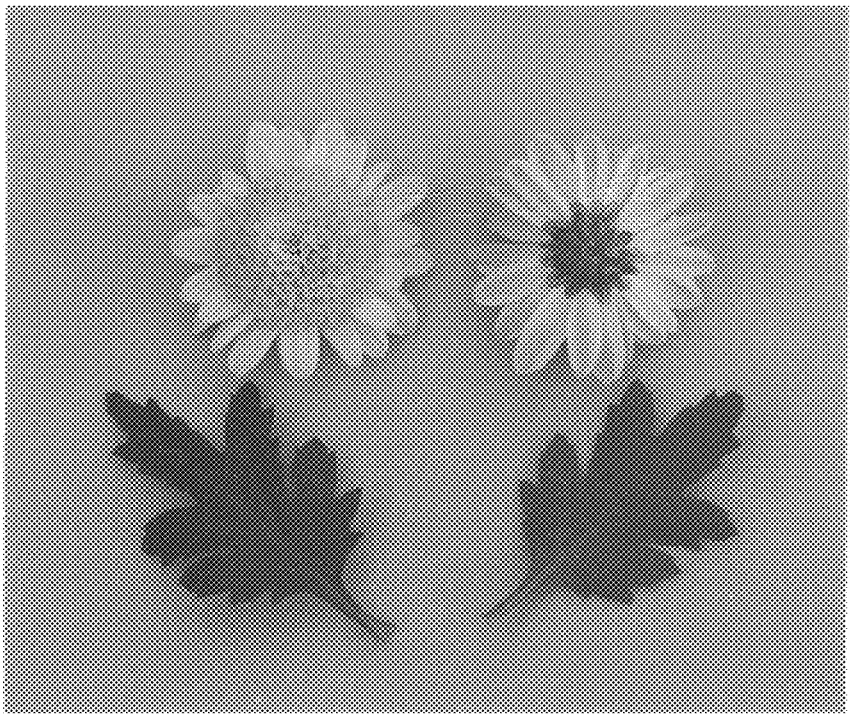
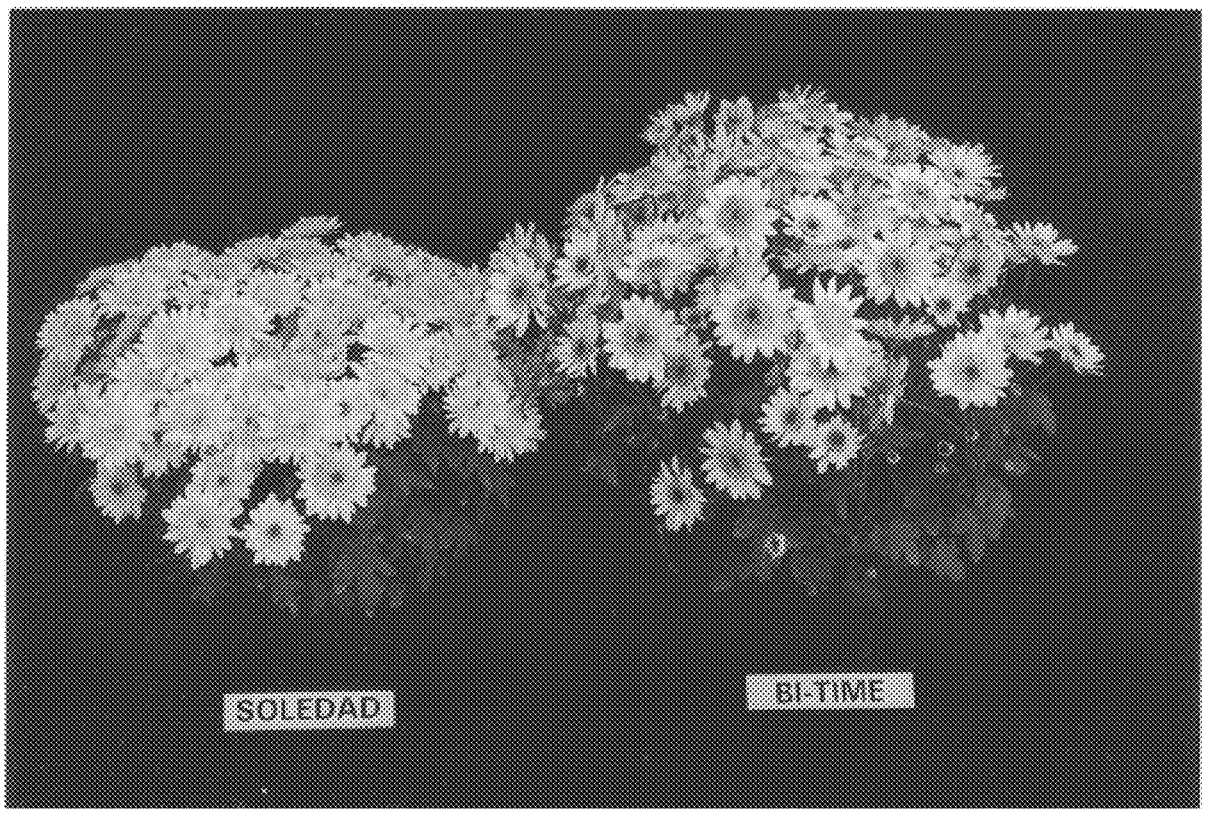
SOLEDAD
BI-TIME